United States Patent
Anilkumar et al.

(10) Patent No.: US 7,967,964 B2
(45) Date of Patent: Jun. 28, 2011

(54) SINGLE CELL SENSOR FOR MEASURING THE PARTIAL PRESSURE OF OXYGEN

(75) Inventors: Ramsesh Anilkumar, Bangalore (IN); Peter J. M. Kroot, Nuenen (NL); Baburaj Kaimalilputhenpura Prabhakaran, Bangalore (IN); Vishal Malhan, Bangalore (IN); Palani Thanigachalam, Bangalore (IN)

(73) Assignee: Honeywell International Inc., Morristown, NJ (US)

( * ) Notice: Subject to any disclaimer, the term of this patent is extended or adjusted under 35 U.S.C. 154(b) by 1149 days.

(21) Appl. No.: 11/711,251

(22) Filed: Feb. 27, 2007

(65) Prior Publication Data

US 2008/0206108 A1 Aug. 28, 2008

(51) Int. Cl.
*G01N 27/417* (2006.01)

(52) U.S. Cl. ..... 204/425; 204/424; 204/426; 205/783.5; 205/784; 205/785; 73/23.31; 73/23.32

(58) Field of Classification Search .......... 204/424–429; 205/783.5–785, 781; 73/23.31–23.32
See application file for complete search history.

(56) References Cited

U.S. PATENT DOCUMENTS

| | | | |
|---|---|---|---|
| 4,272,329 A | 6/1981 | Hetrick et al. | |
| 4,272,331 A | 6/1981 | Hetrick | |
| 4,384,935 A | 5/1983 | De Jong | 204/406 |
| 4,545,889 A | 10/1985 | Franx | 204/406 |
| 4,900,425 A | 2/1990 | Sasayama et al. | |
| 5,516,410 A * | 5/1996 | Schneider et al. | 204/426 |
| 2002/0100698 A1 | 8/2002 | Detwiler et al. | |
| 2002/0175077 A1* | 11/2002 | Wahl et al. | 204/424 |
| 2005/0284772 A1* | 12/2005 | Farber | 205/775 |

FOREIGN PATENT DOCUMENTS

EP 0166530 B1 3/1989

OTHER PUBLICATIONS

Oxygen Sensors, NGK/NTK.
Oxygen Sensors, Service Tech Magazine, May 2001.
High Accuracy Oxygen Sensors, Sensing and Control, Interactive Catalog, Honeywell, Jun. 2004.

* cited by examiner

*Primary Examiner* — Nam X Nguyen
*Assistant Examiner* — Bach T Dinh

(57) ABSTRACT

A single cell oxygen sensor apparatus and method are disclosed. An yttrium-based stabilized layer having electrical terminals connected to the yttrium-based stabilized layer can be provided on a substrate, wherein the yttrium-based stabilized layer is excitable by a constant current applied to the electrical terminals. A plurality of electrodes are located on a side of the yttrium-based stabilized layer and a plurality of heater elements located on said substrate opposite said yttrium-based stabilized layer. The heater elements can maintain the yttrium-based stabilized layer at a particular temperature. A cavity is formed and located between the yttrium-based stabilized layer and the heater elements. The partial pressure of oxygen can be measured by comparing the partial pressure of oxygen within the cavity with respect to the partial pressure of oxygen in the atmosphere external to the single cell oxygen sensor apparatus.

20 Claims, 5 Drawing Sheets

US 7,967,964 B2

SINGLE CELL SENSOR FOR MEASURING THE PARTIAL PRESSURE OF OXYGEN

TECHNICAL FIELD

Embodiments are generally related to sensor devices and techniques. Embodiments are also related to pressure sensors. Embodiments are additionally related to $O_2$ pressure sensors. Embodiments are also related to sensors utilized in engine control applications.

BACKGROUND

Gas sensor devices are utilized in a number of sensing applications. Dual-cell gas sensors, for example, are frequently used to measure oxygen, which is particularly important in automobile and engine systems. One type of dual-cell gas sensor measures the concentration of a gas component in a first space comprising a sealed measurement space, of which at least one wall portion consists of a separation wall which exhibits ionic conduction and is in contact at least in part via the outer side with the first space. In this type of dual-cell gas sensor, a control unit can be utilized to periodically supply during a pumping time interval, a pumping current to the separation wall so that by means of an ion current in the separation wall the gas component is removed from the measurement space.

In this type of device, during a filling time interval a filling current can be supplied whose polarity is opposite to that of the pumping current so that the gas component is supplied to the measurement space. The dual-cell sensor includes a detection circuit which is connected to electrode layers on either side of the separation wall, the outer electrode layer of which is in contact with the first space. This detection circuit includes a first voltage detector, which supplies a filling interrupt signal for interrupting the filling current when the electrode voltage across the said electrode layers reaches a first reference value, and a second voltage detector which supplies a pumping interrupt signal for interrupting the pumping current when the electrode voltage reaches a second reference value. The electrical charge provided in the separation wall is a measure of the concentration of the gas component. Such a gas analysis apparatus is disclosed in U.S. Pat. No. 4,384,935 entitled "Gas Analysis Apparatus" which is incorporated herein by reference.

During the measurement of the electrical charge provided in the separation wall it is assumed that the separation wall, as to its impedance, acts as an electrical resistance so that this charge is to be measured outside the separation wall as supplied and removed charge or as a product of a current to be measured and a time interval to be measured or with constant currents as time intervals.

However, when the various parameters, such as the temperature, the volume of the sealed measurement space, the chosen measurement currents and the measuring range of the concentration to be measured, have such values that the measured time intervals become comparatively small, it is found that the measurement is strongly influenced by switch-on and switch-off transients. In other words, the separation wall is not a pure resistance. It can be derived from a theoretical consideration that the equivalent circuit diagram of the separation wall comprises besides resistances also capacitances, as a result of which RC time constants and stored capacitor charges are obtained.

Another type of dual-cell sensing device is disclosed in U.S. Pat. No. 4,545,889 entitled "Gas Analysis Apparatus" which describes a gas analysis apparatus for measuring the concentration of a gas component in a first space. The apparatus described in U.S. Pat. No. 4,545,889 includes a sealed measurement space, of which at least one wall portion consists of a separation wall which exhibits ionic conduction. The concentration of the gas component in the measurement space is changed periodically between two values by filling and pumping currents at the separation wall. The time intervals are measured and are a measure of the concentration. However, these time intervals comprise a "dead time" caused by switch-on and switch-off (both electrical and physical) transients. When given time intervals are combined by addition and subtraction, the influence of dead times can be considerably reduced using the device of U.S. Pat. No. 4,545,889.

Such dual-cell type sensor devices, however, are plagued with a number of problems. First, a typical dual cell pellet type configuration is designed for flue gas environment and must be redesigned for automotive applications. Thus, the use of dual-cell type sensing devices in automotive applications is very limited. The cost of such sensors is also extremely high, particularly in the context of automotive engine control applications. Dual cell sensors are also bulky and offer a slow response, which means that such devices need to be improved considerably for engine control applications. Additionally, these type of devices are fragile and utilize glass and/or ceramic seals, which are also delicate components, which means that the devices must be re-designed for automotive applications.

It is therefore believed that a solution to these problems lies in eliminating the dual-cell nature of such devices and completely re-designing a much simpler and efficient device, one which is based on the use of a single cell sensing element for oxygen sensing applications. Such a device and operating method are described in greater detail herein.

BRIEF SUMMARY

The following summary is provided to facilitate an understanding of some of the innovative features unique to the embodiments and is not intended to be a full description. A full appreciation of the various aspects of the embodiments disclosed can be gained by taking the entire specification, claims, drawings, and abstract as a whole.

It is, therefore, one aspect of the present invention to provide for an improved pressure sensor.

It is yet another aspect of the present invention to provide for an improved $O_2$ pressure sensor.

It is a further aspect of the present invention to provide for an improved sensor for use in engine control applications.

It is an additional aspect of the present invention to provide for a single cell YSZ (Yttrium stabilized $ZrO_2$) sensor and method for forming and operating the same.

The aforementioned aspects of the invention and other objectives and advantages can now be achieved as described herein. A single cell oxygen sensor apparatus and method are disclosed. In general, an yttrium-based stabilized layer is formed on a substrate and includes electrical terminals connected. The yttrium-based stabilized layer is excitable by a constant current applied to the electrical terminals. A plurality of electrodes are located on one or more sides of the yttrium-based stabilized layer and a plurality of heater elements are located on said substrate opposite said yttrium-based stabilized layer. The heater elements can maintain the yttrium-based stabilized layer at a particular temperature.

A cavity can be formed and located between the yttrium-based stabilized layer and the heater elements. The cavity maintains an oxygen; however, the constant current applied to the electrical terminals results in an immediate evacuation of the oxygen from the cavity, which permits the partial pressure of the oxygen in the cavity to be measured by halting an excitation of the constant current utilizing a fixed resistance across the electrical terminals when a voltage across the yttrium-based stabilized layer attains a particular preset value. The voltage across the yttrium-based stabilized layer and ionic leakage of the oxygen through the yttrium-based stabilized layer then decreases, which permits a measurement of a voltage decay across the yttrium-based stabilized layer to be taken and the partial pressure of the oxygen in the cavity determined with respect to a partial pressure of the oxygen in an atmosphere external to the single cell oxygen sensor apparatus. The voltage decay across the yttrium-based stabilized layer is based on a time taken by a voltage across the yttrium-based stabilized layer to decay from a particular voltage value to another voltage value as a function of a different in a partial pressure of the oxygen between the cavity and the atmosphere. The yttrium-based stabilized layer can be provided as an YSZ (Yttrium stabilized $ZrO_2$) layer.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the principles of the disclosed embodiments.

DETAILED DESCRIPTION

The particular values and configurations discussed in these non-limiting examples can be varied and are cited merely to illustrate at least one embodiment and are not intended to limit the scope of the invention.

Figure 1:
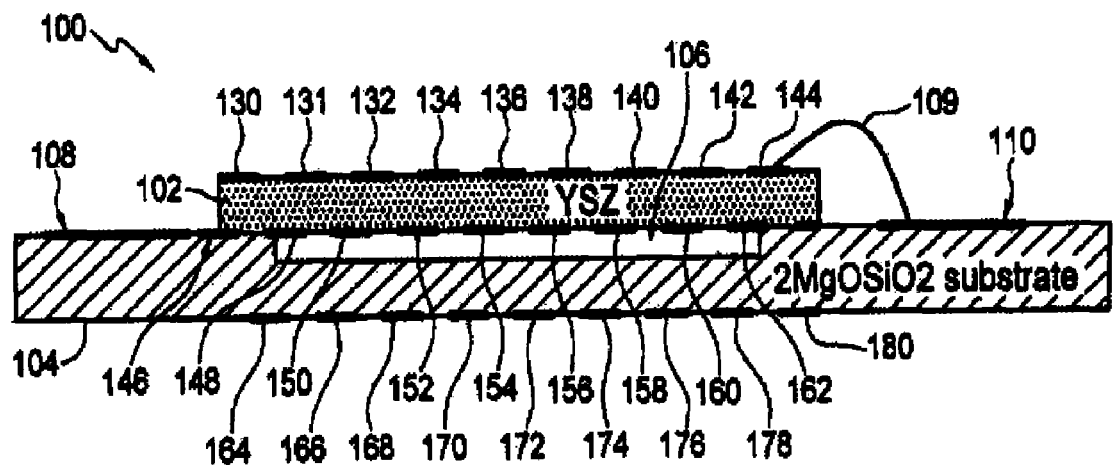
FIG. 1 illustrates a side-view of a single cell oxygen sensor apparatus, which can be implemented in accordance with a preferred embodiment.

FIG. 1 illustrates a side-view of a single cell oxygen sensor apparatus 100, which can be implemented in accordance with a preferred embodiment. The single cell oxygen sensor apparatus 100 depicted in FIG. 1 includes a substrate 104 upon which a layer 102 of Yttrium stabilized $ZrO_2$ can be located. A cavity 106 is located and formed between the layer 102 and the substrate 104. One or more porous platinum electrodes 130, 131, 132, 134, 136, 138, 140, 142, and 144 can be formed on one side of the layer 102, while another set of platinum electrodes 146, 148, 150, 152, 154, 156, 158, 160, and 162 can be formed on the other side of the layer 102.

A group of heater elements 164, 166, 168, 170, 172, 174, 176, 178, and 180 can be formed on a side of the substrate 104 opposite the layer 102 as depicted in FIG. 1. A first terminal 110 can be located on substrate 104 in additional to a second terminal 108. An electrical connector 109 can be utilized to electrically connect terminal 110 to one or more of the electrodes 130, 131, 132, 134, 136, 138, 140, 142, and 144 associated with the layer 102. The substrate 104 can be preferably formed from a material such as, for example, $2MgOSiO_2$, depending upon design consideration.

Figure 2:
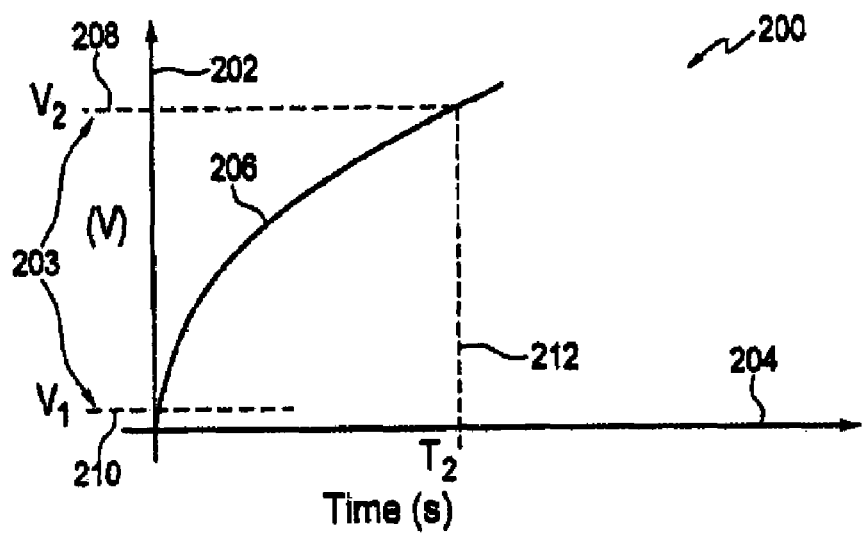
FIG. 2 illustrates a graph depicting a part of the electronic signal sequence for measuring $O_2$ partial pressure around the single cell $O_2$ sensor apparatus, in accordance with a preferred embodiment.

FIG. 2 illustrates a graph 200 depicting a part of the electronic signal sequence for measuring $O_2$ partial pressure around the single cell $O_2$ sensor apparatus 100, in accordance with a preferred embodiment. Graph 200 illustrates a representative curve 206, which represents the voltage across $ZrO_2$ when excited by a constant current. Graph 200 includes a vertical axis 202 indicative of voltage and a horizontal axis 204 indicative of time. A first voltage 210 or $V_1$ and a second voltage 208 or $V_2$ is shown along the vertical axis 202. A second time 212 or $T_2$ is shown on the horizontal axis 204. The voltage difference 203 or V represents the voltage between the first voltage 210 or $V_1$ and the second voltage 208 or $V_2$.

Figure 3:
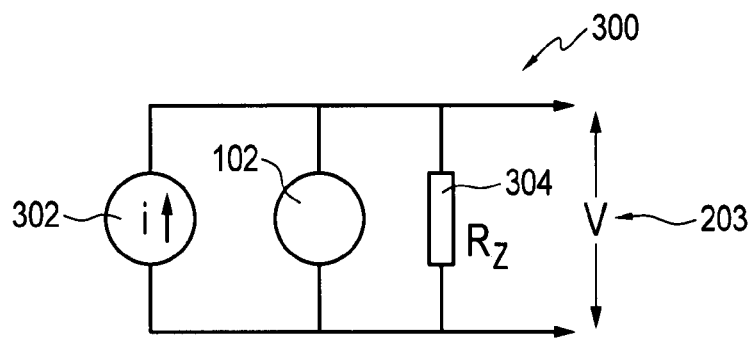
FIG. 3 illustrates a schematic circuit of a circuit representative of electrical activities associated with the single cell oxygen sensor apparatus depicted in FIG. 1 and graph depicted in FIG. 2, in accordance with a preferred embodiment.

FIG. 3 illustrates a schematic circuit of a circuit 300 representative of electrical activities associated with the single cell oxygen sensor apparatus 100 depicted in FIG. 1 and graph 200 depicted in FIG. 2, in accordance with a preferred embodiment. Note that in FIGS. 1-7 illustrated herein, identical or similar parts or elements are generally indicated by identical reference numerals. Thus, circuit 300 includes a constant current source (e.g., 40 μAmps) that is electrically in parallel with the YSZ layer or cell 102 and a resistor 304 or $R_z$. Voltage 203 across the layer or cell 102 is also depicted in circuit 300, which represents an equivalent circuit of the apparatus 100.

In general, the YSZ layer or cell 102 can be excited using the constant current source (DC) 302 through the first and second terminals 110 and 108 in order to pump all O2 from the cavity 106 to the atmosphere (external to the apparatus 100). This "pumping" can be accomplished by monitoring the voltage across the first and second terminals 110 and 108. The voltage across the YSZ layer 102 varies when excited by a constant current and temperature as shown in graph 200 if FIG. 2. At the time $T_2$ where the voltage is $V_2$, the $O_2$ in the cell will be as minimal as possible as it is excited in order to be pumped out of cavity 106. Circuit 300 represents the equivalent electrical circuit of apparatus 100.

Figure 4:
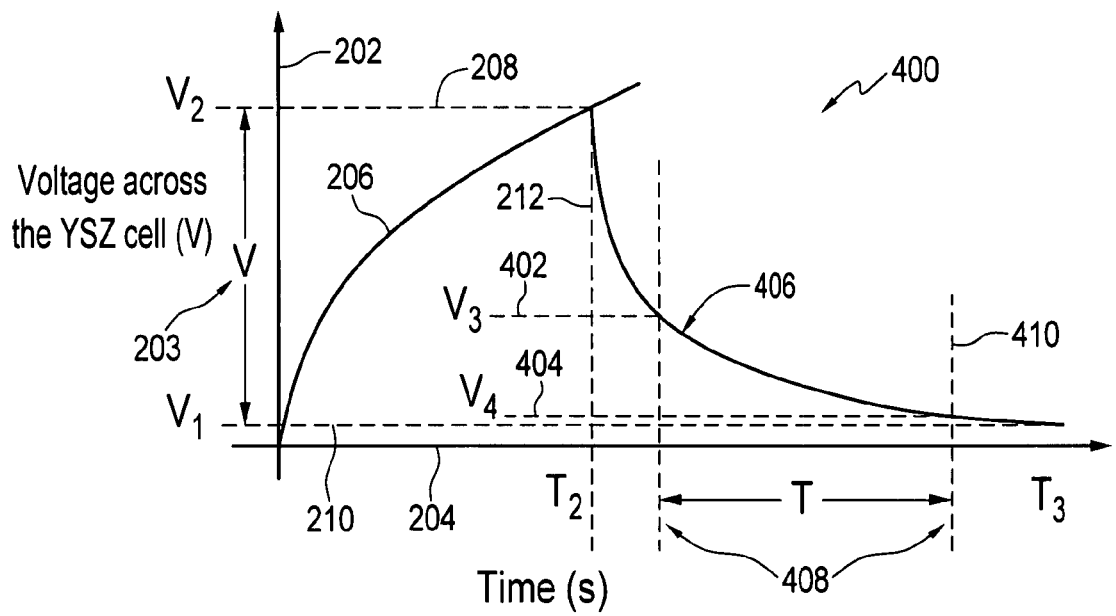
FIG. 4 illustrates a graph indicating the voltage across $ZrO_2$ when loaded with a fixed resistor, in accordance with a preferred embodiment.

FIG. 4 illustrates a graph 400 indicating the voltage across $ZrO_2$ when loaded with a fixed resistor, in accordance with a preferred embodiment. Graph 400 is similar to graph 300, the difference being the inclusion of data per the addition of a fixed resistor. Thus, in addition to the parameters indicated in graph 200 of FIG. 2, the graph 400 of FIG. 4 includes third and fourth voltages 402 and 404 (respectively $V_3$ and $V_4$) and second and third times 212 and 410 (respectively $T_2$ and $T_3$). Time 408 (T) depicted in graph 400 represents the time that is proportional to the $O_2$ partial pressure. Additionally, the curve 406 of graph 400 indicates that decay depends on leakage current (i.e., the load resistance).

Figure 5:
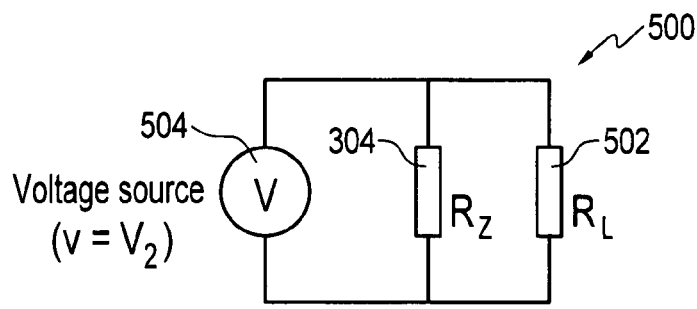
FIG. 5 illustrates an equivalent circuit between a time $T_2$ and $T_3$ discharge cycle, in accordance with a preferred embodiment.

FIG. 5 illustrates an equivalent circuit 500 between a time $T_2$ and $T_3$ discharge cycle, in accordance with a preferred embodiment. Circuit 500 represents an equivalent circuit of apparatus 100. FIG. 5 includes a voltage source 504 (i.e., $v=V_2$) in parallel with resistor 304 ($R_z$) and a load resistor 502 ($R_L$). The resistor 304 ($R_z$) represents the YSZ internal resistance at a particular temperature and the load resistor 502 ($R_L$) is the external load resistor to drive current.

Thus, at the pre-defined value of voltage ($V_2$), the constant current is switched off and a fixed resistor is connected across the first and second sensor terminals 110 and 108, which will act to induce ionic/electrical leakage and thus the voltage across the sensor element drops down as shown in graph 400 of FIG. 4. The equivalent circuit at this condition is as shown in circuit 500 of FIG. 5.

The decay time from $V_3$ to $V_4$ (i.e., Time ($T_3-T_2$)) is the time proportional to the $O_2$ partial pressure difference between the cavity 106 and the surrounding area of the sensor 100. If the $O_2$ Partial pressure inside the cavity 106 is zero or close to zero at time $T_2$ (i.e. when the voltage across the sensor is $V_2$), then the signal is proportional to the $O_2$ partial pressure around the sensor element or YSZ cell 102.

Figure 6:
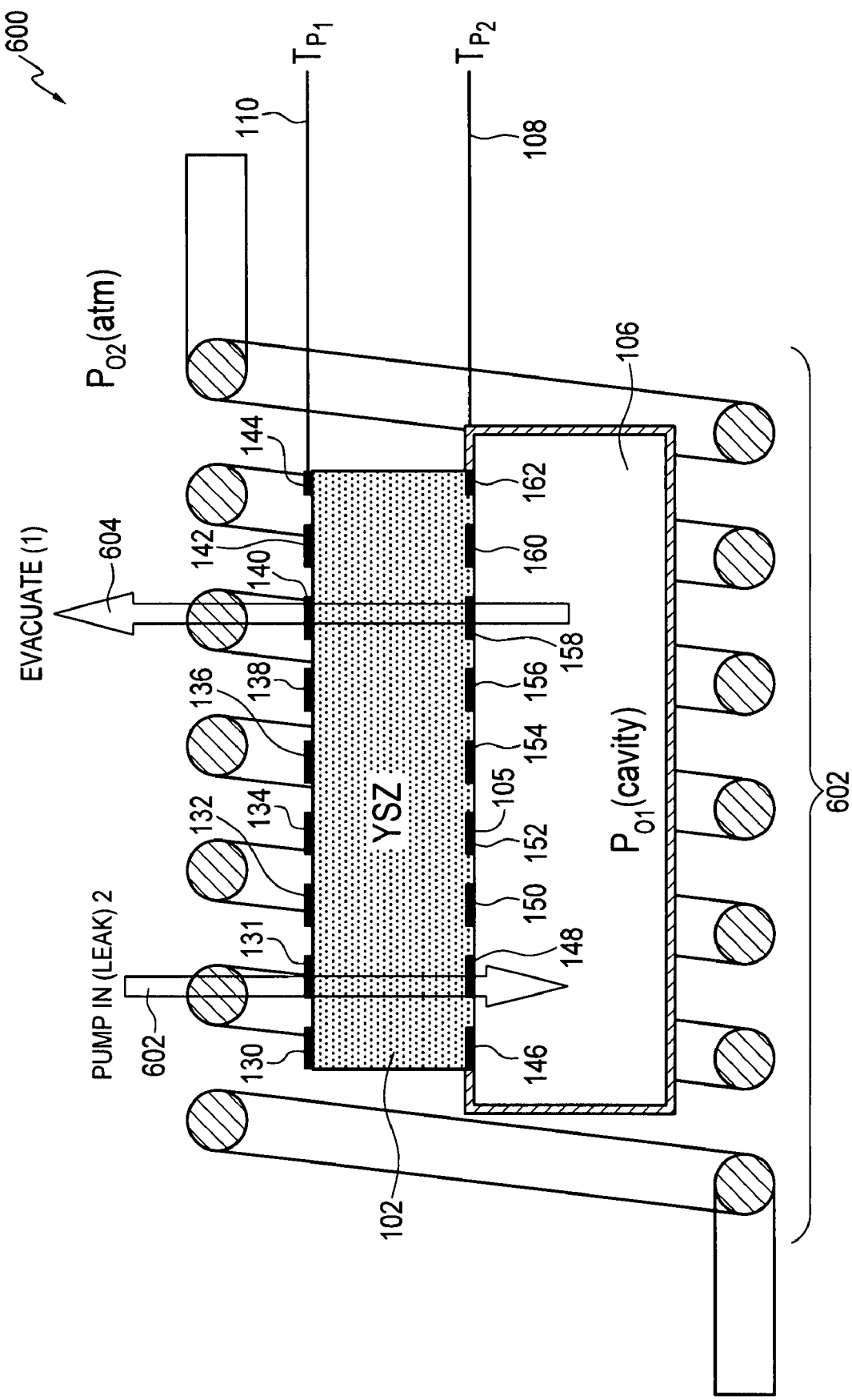
FIG. 6 illustrates a side-view of a single cell oxygen sensor apparatus, which can be implemented in accordance with an alternative embodiment.

FIG. 6 illustrates a side-view of a single cell oxygen sensor apparatus 600, which can be implemented in accordance with an alternative embodiment. The sensor apparatus 600 depicted in FIG. 6 is similar to that of the sensor apparatus 100, with slight differences. For example, electrodes 146, 148, 150, 152, 154, 156, 158, 160, and 162 are illustrated in FIG. 6. As indicated in FIG. 6, a heater 602 is associated with cavity 106. The heater 602 can be composed of, for example, one or more group of heater elements 164, 166, 168, 170, 172, 174, 176, 178, which were depicted earlier with respect to FIG. 1. Arrows 604 and 602 respectively represent oxygen evacuation and heat pumped into cavity 106.

Figure 7:
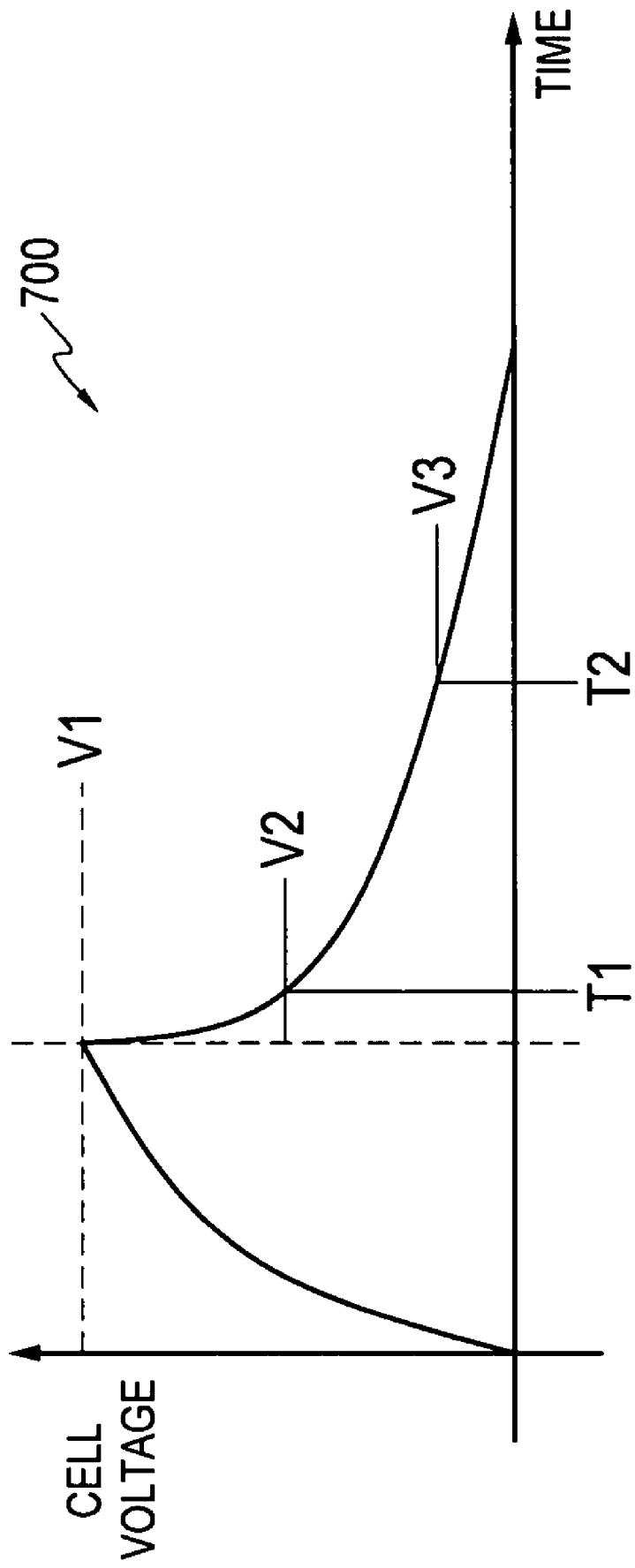
FIG. 7 illustrates a graph associated with the operation of sensor apparatus of FIGS. 1 and/or 6 and indicating that the time T is a function of the difference in $O_2$ partial pressures between the atmosphere and the cavity.
Figure 8:
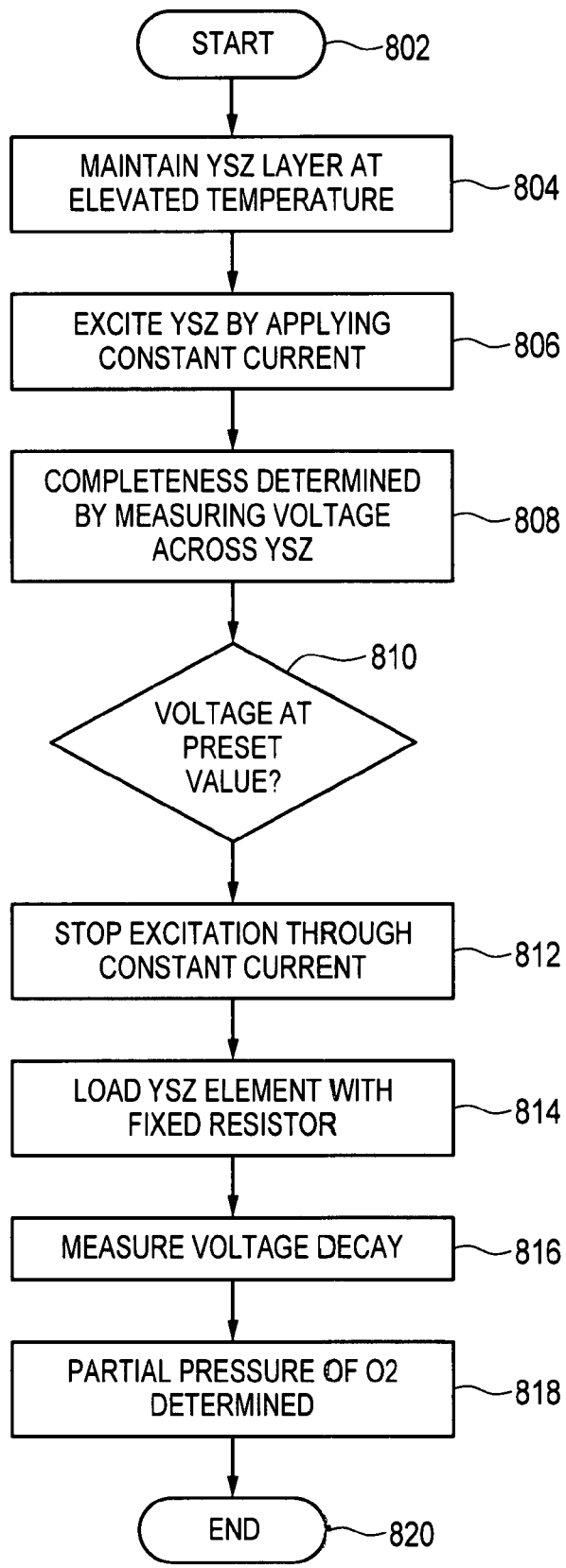
FIG. 8 illustrates a high-level flow chart of operations of a method that can be followed in order to operate the sensor apparatus of FIGS. 1 and/or 6, in accordance with preferred or alternative embodiments.

FIG. 7 illustrates a graph 700 associated with the operation of sensor apparatus 600 and indicating that the time T is a function of the difference in $O_2$ partial pressures between the atmosphere and the cavity 106. The following parameters and variable apply to the illustration depicted in FIG. 6 and graph 700 of FIG. 7:

YSZ—Yttrium stabilized $ZrO_2$
Pt—platinum electrodes
$P_{O2}$ (atm)—Partial pressure of $O_2$ in atmosphere
$P_{O1}$ (cavity)—partial pressure of $O_2$ in cavity
Tp1 and Tp2 are terminals across YSZ FIG. 8 illustrates a high-level flow chart of operations of a method 800 that can be followed in order to operate the sensor apparatus 100 and sensor apparatus 600, in accordance with preferred or alternative embodiments. The process can begin, as indicated at block 802. As depicted thereafter at block 804, the YSZ layer 102 can be maintained at an elevated temperature (e.g., approximately 700 Deg C., but this depends on the size, temperature, type, etc. of the sensor element). Next, as described at block 806, the YSZ layer or cell 102 can be excited by applying a constant current of 40 mA (depends on the size, temperature, type, etc. of the sensor element) or more or less across terminal Tp1 and Tp2 such that the $O_2$ in the cavity is evacuated completely. The completeness can then be determined as indicated at block 808 by measuring the voltage across YSZ layer or cell 102 (i.e. across terminals Tp1 and Tp2).

Thereafter, as indicated at blocks 810 and 812, when the voltage across the YSZ layer or cell 102 reaches a particular preset value V1 (e.g., 500 mV—fully evacuated condition—see FIG. 2), the excitation is halted through a constant current. The YSZ element can be loaded with a fixed resistor across its terminal sTp1 and Tp2 as indicated at block 814 so that the current flow, the $O_2$ leak through YSZ layer or cell 102 (ionic leakage) and the voltage across the YSZ layer or cell 102 decreases. Next, as indicated at block 816, the voltage decay across the YSZ layer or cell 102 can be measured. The time taken by the voltage to decay from V2 to V3 (e.g., see FIG. 2) is a function of the difference in $O_2$ partial pressure between the cavity 106 and the atmosphere.

Next, as depicted at block 810, if the partial pressure of $O_2$ in the atmosphere is greater than the partial pressure of $O_2$ in cavity 106, the time taken to leak is larger, and if the partial pressure of $O_2$ in atmosphere is smaller or equal to the partial pressure of $O_2$ in cavity 106, the time taken to leak is less. The process can then terminate, as indicated at block 820.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A single cell oxygen sensor apparatus, comprising:
    an sensing layer formed on a $2MgOSiO_2$ substrate, wherein said sensing layer is connected to electrical terminals, such that said sensing layer is excitable by a constant current applied to said electrical terminals;
    a plurality of electrodes located on at least one side of said sensing layer and a plurality of heater elements located on said substrate opposite said sensing layer, wherein said plurality of heater elements maintain said sensing layer at a particular temperature; and
    a cavity formed between said sensing layer and said plurality of heater elements, wherein said constant current applied to said electrical terminals results in an immediate evacuation of oxygen from said cavity, thereby permitting a partial pressure of said oxygen in said cavity to be measured by halting an excitation of said constant current utilizing a fixed resistance across said electrical terminals when a voltage across said sensing layer attains a particular preset value so that a voltage across said sensing layer and ionic leakage of said oxygen through said sensing layer decreases, which permits a measurement of a voltage decay across said sensing layer to be taken and said partial pressure of said oxygen in said cavity determined with respect to a partial pressure of said oxygen in an atmosphere external to said single cell oxygen sensor apparatus.

2. The apparatus of claim 1 wherein said sensing layer comprises an yttrium-based stabilized layer.

3. The apparatus of claim 2 wherein said yttrium-based stabilized layer comprises a YSZ layer.

4. The apparatus of claim 1 wherein said constant current comprises a current of approximately 40 μAmps.

5. The apparatus of claim 1 wherein said particular temperature maintained by said plurality of heater elements comprises an elevated temperature of approximately 700° C.

6. The apparatus of claim 1 wherein said voltage decay across said sensing layer is based on a time taken by said voltage across said sensing layer to decay from a particular voltage value to another voltage value as a function of a different in a partial pressure of said oxygen between said cavity and said atmosphere.

7. A single cell oxygen sensor apparatus, comprising:
    a sensing layer formed on a $2MgOSiO_2$ substrate, wherein said sensing layer is connected to electrical terminals, such that said sensing layer is excitable by a constant current applied to said electrical terminals and wherein said sensing layer comprises an yttrium-based stabilized layer;

a plurality of electrodes located on at least one side of said sensing layer and a plurality of heater elements located on said substrate opposite said sensing layer, wherein said plurality of heater elements maintain said sensing layer at a particular temperature; and a cavity formed between said sensing layer and said plurality of heater elements, wherein said constant current applied to said electrical terminals results in an immediate evacuation of oxygen from said cavity, thereby permitting a partial pressure of said oxygen in said cavity to be measured by halting an excitation of said constant current utilizing a fixed resistance across said electrical terminals when a voltage across said sensing layer attains a particular preset value so that a voltage across said sensing layer and ionic leakage of said oxygen through said sensing layer decreases, which permits a measurement of a voltage decay across said sensing layer to be taken and said partial pressure of said oxygen in said cavity determined with respect to a partial pressure of said oxygen in an atmosphere external to said single cell oxygen sensor apparatus.

8. The apparatus of claim 7 wherein said yttrium-based stabilized layer comprises a YSZ layer.

9. The apparatus of claim 7 wherein said constant current comprises a current of approximately 40 µAmps.

10. The apparatus of claim 7 wherein said particular temperature maintained by said plurality of heater elements comprises an elevated temperature of approximately 700° C.

11. The apparatus of claim 7 wherein said voltage decay across said sensing layer is based on a time taken by said voltage across said sensing layer to decay from a particular voltage value to another voltage value as a function of a different in a partial pressure of said oxygen between said cavity and said atmosphere.

12. A single cell oxygen sensor apparatus, comprising:
an sensing layer formed on a $2MgOSiO_2$ substrate, wherein said sensing layer is connected to electrical terminals, such that said sensing layer is excitable by a constant current applied to said electrical terminals;

a plurality of electrodes located on at least one side of said sensing layer and a plurality of heater elements located on said substrate opposite said sensing layer, wherein said plurality of heater elements maintain said sensing layer at a particular temperature; and a cavity formed between said sensing layer and said plurality of heater elements, wherein said constant current applied to said electrical terminals results in an immediate evacuation of said oxygen from said cavity, thereby permitting a partial pressure of said oxygen in said cavity to be measured by halting an excitation of said constant current utilizing a fixed resistance across said electrical terminals when a voltage across said sensing layer attains a particular preset value so that a voltage across said sensing layer and ionic leakage of said oxygen through said sensing layer decreases, which permits a measurement of a voltage decay across said sensing layer to be taken and said partial pressure of said oxygen in said cavity determined with respect to a partial pressure of said oxygen in an atmosphere external to said single cell oxygen sensor apparatus and wherein said voltage decay across said sensing layer is based on a time taken by said voltage across said sensing layer to decay from a particular voltage value to another voltage value as a function of a different in a partial pressure of said oxygen between said cavity and said atmosphere.

13. The apparatus of claim 1 wherein said sensing layer comprises an yttrium-based stabilized layer.

14. The apparatus of claim 2 wherein said yttrium-based stabilized layer comprises a YSZ layer.

15. A method of configuring a single cell oxygen sensor apparatus, comprising:
forming a sensing layer on a $2MgOSiO_2$ substrate, wherein said sensing layer is connected to electrical terminals, such that said sensing layer is excitable by a constant current applied to said electrical terminals;

locating a plurality of electrodes on at least one side of said sensing layer and a plurality of heater elements located on said substrate opposite said sensing layer, wherein said plurality of heater elements maintain said sensing layer at a particular temperature; and forming a cavity between said sensing layer and said plurality of heater elements, wherein said constant current applied to said electrical terminals results in an immediate evacuation of oxygen from said cavity, thereby permitting a partial pressure of said oxygen in said cavity to be measured by halting an excitation of said constant current utilizing a fixed resistance across said electrical terminals when a voltage across said sensing layer attains a particular preset value so that a voltage across said sensing layer and ionic leakage of said oxygen through said sensing layer decreases, which permits a measurement of a voltage decay across said sensing layer to be taken and said partial pressure of said oxygen in said cavity determined with respect to a partial pressure of said oxygen in an atmosphere external to said single cell oxygen sensor apparatus.

16. The method of claim 15 further comprising configuring said sensing layer to comprise an yttrium-based stabilized layer.

17. The method of claim 16 wherein said yttrium-based stabilized layer comprises a YSZ layer.

18. The method of claim 15 wherein further comprising providing said constant current as a current of approximately 40 µAmps.

19. The method of claim 15 wherein further comprising establishing said particular temperature maintained by said plurality of heater elements to comprise an elevated temperature of approximately 700° C.

20. The method of claim 15 wherein said voltage decay across said sensing layer is based on a time taken by said voltage across said sensing layer to decay from a particular voltage value to another voltage value as a function of a different in a partial pressure of said oxygen between said cavity and said atmosphere.

* * * * *